United States Patent [19]

Grunberg et al.

[11] 3,962,435

[45] June 8, 1976

[54] COMBINATION OF OXYTETRACYCLINE AND 2,4-DIAMINO-5-(3-ALKOXY-4,5-METHYLENEDIOXYBENZYL)PYRIMIDINE

[75] Inventors: Emanuel Grunberg, North Caldwell; Max Hoffer, Nutley, both of N.J.

[73] Assignee: Hoffmann-La Roche Inc., Nutley, N.J.

[22] Filed: Dec. 9, 1974

[21] Appl. No.: 531,135

Related U.S. Application Data

[62] Division of Ser. No. 404,953, Oct. 10, 1973, which is a division of Ser. No. 203,869, Dec. 1, 1971, Pat. No. 3,787,409.

[52] U.S. Cl. ............................. 424/227; 424/251
[51] Int. Cl.² .................................. A61K 31/65
[58] Field of Search ..................... 424/251, 227

[56] References Cited

UNITED STATES PATENTS 3,787,409   1/1974   Grunberg et al. .................. 424/251

*Primary Examiner*—Jerome D. Goldberg
*Attorney, Agent, or Firm*—Samuel L. Welt; George M. Gould; William G. Isgro

[57] ABSTRACT

2,4-Diamino-5-(3-alkoxy-4,5-methylenedioxybenzyl)-pyrimidines, such as, for example, 2,4-diamino-5-(3-methoxy-4,5-methylenedioxybenzyl)pyrimidine, prepared from the corresponding benzaldehydes, are described. The end products are useful as potentiators of the antibacterial activity of sulfonamides, as well as antibiotics.

3 Claims, No Drawings

COMBINATION OF OXYTETRACYCLINE AND 2,4-DIAMINO-5-(3-ALKOXY-4,5-METHYLENEDIOXYBENZYL)PYRIMIDINE

CROSS-REFERENCE TO RELATED APPLICATIONS

This application is a division of U.S. patent application Ser. No. 404,953, filed Oct. 10, 1973, which in turn is a Rule 60 Division of U.S. patent application Ser. No. 203,869, filed Dec. 1, 1971, now U.S. Pat. No. 3,787,409, issued Jan. 22, 1974.

BRIEF SUMMARY OF THE INVENTION

The invention relates to compounds characterized by the formula

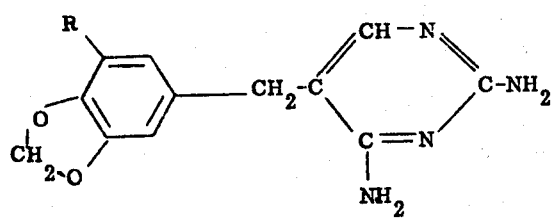

wherein R is lower alkoxy, and addition salts thereof with pharmaceutically acceptable acids. The compounds of formula I are useful as potentiators of the antibacterial activity of sulfonamides, as well as antibiotics.

DETAILED DESCRIPTION OF THE INVENTION

The invention relates to compounds characterized by the formula

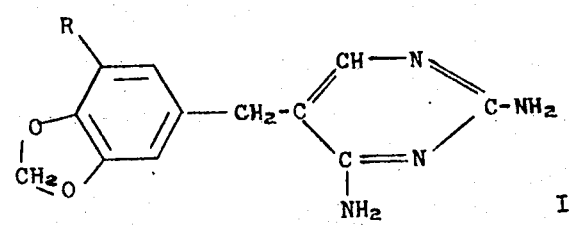

wherein R is lower alkoxy, which preferably has from 1 to 7 carbon atoms, for example, methoxy, ethoxy, propoxy, butoxy, pentoxy, and the like.

The most preferred embodiment of the invention is 2,4-diamino-5-(3-methoxy-4,5-methylenedioxybenzyl)pyrimidine.

The compounds of formula I are prepared in accordance with the process illustrated by the following reaction scheme:

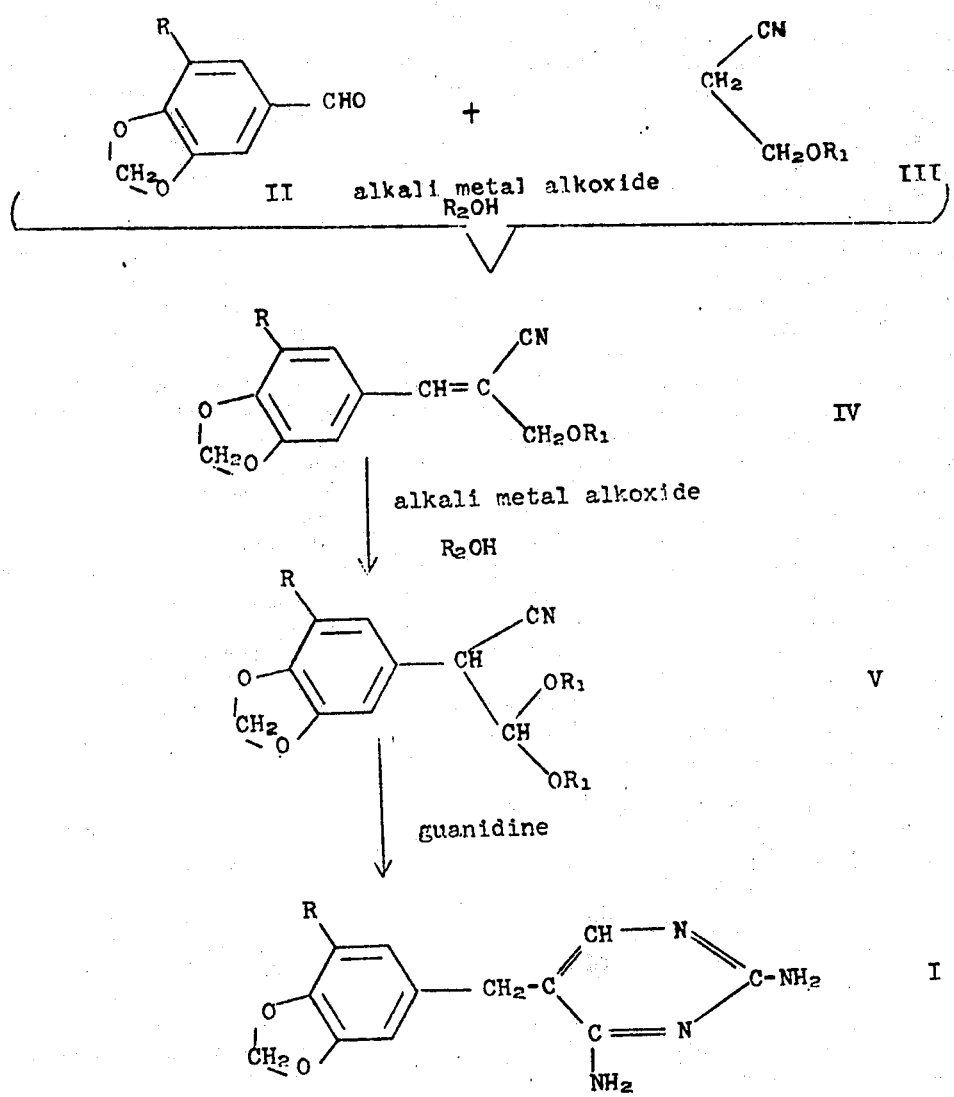

wherein R is as previously described and $R_1$ and $R_2$ are lower alkyl of 1-7 carbon atoms; methyl is preferred.

The foregoing reaction is carried out by first reacting an aldehyde of formula II with a β-lower alkoxy propionitrile of formula III in the presence of an alkali metal lower alkoxide, such as sodium methoxide, potassium ethoxide, etc. and a lower alkanol of the formula $R_2OH$, e.g., methanol, ethanol, propanol, etc. The reaction temperature is not critical, but it is generally in the range of about 60° to about 140°C. The reaction product obtained is a compound of formula IV which is readily converted into a compound of formula V by treatment with $R_2OH$ in the presence of an alkali metal lower alkylate under substantially anhydrous conditions. The reaction temperature is also not critical for this step, and temperatures of about 60° to about 140°C. are suitable here also. A compound of formula V is then reacted with guanidine, in the presence of a solvent, if required, to give an almost quantitative yield of a compound of formula I.

The aldehydes of formula II are known compounds or can readily be prepared by known techniques, for example, by the Rosenmund method (Organic Synthesis, I.C., p. 1332), or by the method of W. Bonthrone and J. W. Cornforth, J. Chem. Soc. (c) 1202 (1969).

The compounds of formula I form acid addition salts and such salts are also within the scope of this invention. Thus, the compounds of formula I form pharmaceutically acceptable addition salts with, for example, both pharmaceutically acceptable organic and inorganic acids, such as acetic acid, succinic acid, formic acid, methanesulfonic acid, p-toluene-sulfonic acid, hydrochloric acid, nitric acid, phosphoric acid, sulfuric acid, lactic acid, and the like.

The compounds of formula I are useful in combination with one or more sulfa drugs, such as, for example, $N^1$-(3,4-dimethyl-5-isoxazolyl)-sulfanilamide, 5-methyl-3-sulfanilamido-isoxazole, $N^1$-(2,6-dimethoxy-4-pyrimidinyl)-sulfanilamide, $N^4$-ethoxyacetyl-$N^1$-(5-methyl-3-isoxazolyl)-sulfanilamide, $N^1$-(4,5-dimethyl-3-isoxazolyl)-sulfanilamide, $N^1$-(5,6-dimethoxy-4-pyrimidinyl)-sulfanilamide, and the like, as antibacterial agents. The addition of a compound of formula I to one of the above-mentioned sulfonamides results in a marked potentiation of the anti-bacterial activity of the sulfonamide. Thus, the compounds of formula I are useful as potentiators of sulfonamides. The combination of a compound of formula I and a sulfonamide is prepared simply by admixture, which can ultimately be embodied into a suitable oral dosage form, as hereinafter described. Unexpectedly, the compounds of formula I also potentiate the anti-bacterial activity of antibiotics, such as, for example, oxytetracycline, penicillin and the like. Thus, the compounds of formula I are also useful as potentiators of antibiotics. The combination of a compound of formula I and an antibiotic is prepared simply by admixture, which can ultimately be embodied into a suitable oral dosage form, as hereinafter described.

The ratios in which a therapeutically active compound of formula I and a sulfonamide are utilized can be varied within wide limits. For example, the combination can contain from about 1 to about 50 parts, preferably from about 1 to about 20 parts, of sulfonamide or an equivalent amount of salt thereof to one part of a compound of formula I or equivalent amount of salt thereof.

The ratios in which a therapeutically active compound of formula I and an antibiotic are utilized can be varied within wide limits. For example, the combination can contain from about 1 to about 50 parts, preferably from about 1 to about 20 parts, of antibiotic or an equivalent amount of salt thereof to one part of a compound of formula I or equivalent amount of salt thereof.

The products of the invention can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols, and the like. The pharmaceutical preparations can be employed in a solid form, for example, as tablets, troches, suppositories, capsules or in liquid form, for example, as solutions, suspensions or emulsions. The pharmaceutical adjuvant material can be added and can include preservatives, stabilizers, wetting or emulsifying agents, salts to change the osmotic pressure or to act as buffers. They can also contain other therapeutically active materials. The combination of a compound of formula I and a sulfonamide can be administered in unit dosage forms which contain 500 mg. of sulfonamide or an equivalent amount of a salt thereof and from about 10 mg. to about 100 mg. of a compound of formula I or an equivalent amount of a salt thereof. However, it is also within the scope of the invention to utilize a unit dosage form which will contain from about 250 mg. to about 750 mg. of sulfonamide or equivalent amount of a salt thereof and from about 5 mg. to about 150 mg. of a compound of formula I or equivalent amount of a salt thereof.

The combination of a compound of formula I and an antibiotic can be administered in dosage forms which contain 250 mg. of antibiotic or an equivalent amount of a salt thereof and from about 5 mg. to about 50 mg. of a compound of formula I or an equivalent amount of a salt thereof. However, it is also within the scope of the invention to utilize a unit dosage form which will contain from about 250 mg. to about 750 mg. of antibiotic or equivalent amount of a salt thereof and from about 5 mg. to about 150 mg. of a compound of formula I or an equivalent amount of salt thereof.

The frequency with which any such unit dosage will be administered to a warm-blooded animal will vary, depending upon the quantity of medicament present therein and the needs and requirements of the warm-blooded animal.

The sulfonamides hereinbefore described form salts with pharmaceutically acceptable bases, for example, they form salts with alkali metal bases, such as, for example, sodium hydroxide, potassium hydroxide or the like.

The following examples further illustrate the invention. All parts are by weight and all temperatures are in degrees Centigrade, unless otherwise mentioned.

EXAMPLE 1
Preparation of 3-methoxy-4,5-methylenedioxy-α-methoxymethylcinnamonitrile 3.8 g. of sodium were dissolved in 120 ml. of methanol under reflux. 56 g. of methoxypropionitrile and 60 g. of 3-methoxy-4,5-methylenedioxybenzaldehyde were then added and refluxed in the methanol mixture for 5 hours. Upon chilling, 3-methoxy-4,5-methylenedioxy-α-methoxymethyl-cinnamonitrile crystallized in needles of m.p. = 115°, in a yield of 68 g. = 83 percent. A sample of analysis was recrystallized from methanol, m.p. 115.5°–116.5°.

Analysis - $C_{13}H_{13}NO_4$: Calc'd: C, 63.2; H, 5.26; N, 5.67. Found: C, 63.15; H, 5.22; N, 5.62.

EXAMPLE 2

Preparation of 2,4-diamino-5-(3-methoxy-4,5-methylenedioxybenzyl)pyrimidine 12.8 g. of sodium were dissolved in 185 ml. of methanol, under stirring and reflux. 68 g. of 3-methoxy-4,5-methylenedioxy-α-methoxymethylcinnamonitrile were added and the mixture was refluxed for 48 hours. The reactant dissolved gradually, and the solution darkened. Thereafter, the reaction was quenched with 500 ml. of water and neutralized with 20 ml. of acetic acid, followed by extraction with three portions of benzene, i.e., 600 + 50 + 50 ml. The benzene layer was dried over sodium sulfate and cleared by filtering it through a filter containing charcoal. The solvent was evaporated in vacuo and the residue removed by distillation at 184°–198°, 1.5 mmHg. The product was a viscous colorless oil of $n_D^{22}$ = 1.5320. 41 g. was refluxed with 290 ml. of 1 molar methanolic guanidine solution for 1.5 hours. The methanol was then removed by distillation over an oil bath at 160° and the residue kept at that temperature until it solidified to a crystalline mass (10–15 min.). Thereafter, the product was slurried with water and filtered by suction. Yield of the crude product was 37 g. = 92 percent, m.p. unsharp 215°.

To purify the crude product it was slurried with 120 ml. of acetic acid and heated until it had dissolved. Upon cooling, the acetate crystallized as white needles which were pressed off on a suction filter and dissolved in 250 ml. of hot water. The solution was charcoaled and the 2,4-diamino-5-(3-methoxy-4,5-methylenedioxybenzyl)pyrimidine precipitated with an excess of ammonia, m.p. = 236°–237°, yield 28.5 g. = 70 percent.

Analysis - $C_{13}H_{14}N_4O_3$: Calc'd: C, 56.9; H, 5.11; N, 20.45. Found: C, 56.67; H, 5.27; N, 20.35.

EXAMPLE 3

Preparation of 3-ethoxy-3,4-methylenedioxy-α-methoxymethylcinnamonitrile

To a solution containing 2.16 g. of sodium in 100 ml. methanol, there were added 32 g. of β-methoxypropionitrile and 36.5 g. of 3-ethoxy-4,5-methylenedioxy benzaldehyde. Thereafter, the mixture was refluxed for 6.5 hours. 300 ml. of water were added and the 3-ethoxy-3,4-methylenedioxy-α-methoxymethylcinnamonitrile was extracted with methylenechloride. Upon evaporation of the solvent and vacuum distillation, the 3-ethoxy-3,4-methylenedioxy-α-methoxymethyl-cinnaminonitrile had a b.p. of 175°/0.3 mmHg and m.p. of 64°–65°.

Analysis - $C_{14}H_{15}NO_4$ Calc'd: C, 64.36; H, 5.79; N, 5.36. Found: C, 64.57; H, 5.83; N, 5.28.

EXAMPLE 4

Preparation of 3-ethoxy-4,5-methylenedioxy-α-cyanodihydrocinnamaldehyde dimethylacetal To 6.6 g. sodium dissolved in 96 ml. of methanol, 37.5 g. of 3-ethoxy-4,5-methylenedioxy-α-methoxymethylcinnamonitrile were added. The resulting mixture was refluxed for 24 hours. The solution was poured into 400 ml. water and was extracted with methylenechloride. Upon evaporation of the solvent, the product, 3-ethoxy-4,5-methylenedioxy-α-cyanodihydrocinnamaldehyde dimethylacetal, was vacuum distilled and had a b.p. of 191°/0.4 mmHg., $n_D^{23}$ = 1.5340.

Analysis - $C_{15}H_{19}NO_5$ Calc'd: C, 61.41; H, 6.53; N, 4.78. Found: C, 62.23; H, 6.17; N, 4.78.

EXAMPLE 5

Preparation of 2,4-diamino-5-(3-ethoxy-4,5-methylenedioxybenzyl)-pyrimidine 30.5 g. of 3-ethoxy-4,5-methylenedioxy-α-cyanodihydrocinnamaldehyde dimethylacetal were added to 200 ml. of freshly prepared 0.2 molar solution of guanidine in methanol, and the solvent was gradually removed by distillation over an oil bath at a temperature of 120°–140°. The residue was heated for 10 minutes to 140°–160° and it completely solidified to a crystalline mass. For purification, the mass was dissolved in 100 ml. hot acetic acid and the product allowed to crystallize as an acetate upon chilling. The latter was filtered by suction, dissolved in 400 ml. of hot water and the solution alkalized with ammonia to precipitate 2,4-diamino-5-(3-ethoxy-4,5-methylenedioxybenzyl)-pyrimidine as white crystals of free base having a m.p. of 202.5°–203.5°.

Analysis - $C_{14}H_{16}N_4O_3$ Calc'd: C, 58.32; H, 5.59; N, 19.44. Found: C, 58.51; H, 5.72; N, 19.69.

The starting material 3-ethoxy-4,5-methylenedioxy benzaldehyde was obtained by methylenation of 3-ethoxy-4,5-dihydroxybenzaldehyde essentially by the method of W. Bonthrone and J. W. Cornforth, J. Chem. Soc. (C) 1202 (1969).

White crystals, m.p. of 60°–61°, b.p. of 103°–104°/0.1 mmHg.

Analysis - $C_{10}H_{10}O_4$ Calc'd: C, 61.85; H, 5.19. Found: C, 61.70; H, 5.18.

3-ethoxy-4,5-dihydroxybenzaldehyde was obtained from 3-ethoxy-4-hydroxy-5-bromobenzaldehyde, P. Mariella and J. M. Bauer, J. Org. Chem. 23: 120 (1958) in analogy to Bradley, Robinson and Schwarzenback, J. Chem. Soc. 811 (1930), white crystals, from water, m.p. of 117°–118°.

Analysis - $C_9H_{10}O_4$ Calc'd: C, 59.33; H, 5.53. Found: C, 59.65; H, 5.52.

EXAMPLE 6

Capsule Formulation

|  | Per Capsule |
|---|---|
| $N^1$-(3,4-dimethyl-5-isoxazolyl)-sulfanilamide | 250 mg. |
| 2,4-diamino-5-(3-methoxy-4,5-methylenedioxybenzyl)pyrimidine | 25 mg. |
| Lactose | 68 mg. |
| Corn Starch | 27 mg. |
| Talc | 5 mg. |
| Total weight | 375 mg. |

Procedure:
1. The $N^1$-(3,4-dimethyl-5-isoxazolyl)-sulfanilamide, 2,4-diamino-5-(3-methoxy-4,5-methylenedioxybenzyl)pyrimidine, lactose and corn starch are mixed in a suitable mixer.

2. The mixture is further blended by passing through a comminuting machine with a No. 1A screen with knives forward.

3. The blended powder is returned to the mixer, the talc added and blended thoroughly. The mixture is then filled into No. 4 hard shell gelatin capsules on a capsulating machine.

EXAMPLE 7

Capsule Formulation

|  | Per Capsule |
| --- | --- |
| Oxytetracycline | 250 mg. |
| 2,4-Diamino-5-(3-methoxy-4,5-methylene-dioxybenzyl)-pyrimidine | 25 mg. |
| Lactose | 68 mg. |
| Corn Starch | 27 mg. |
| Talc | 5 mg. |
| Total Weight | 375 mg. |

Procedure:

1. The oxytetracycline, 2,4-diamino-5-(3-methoxy-4,5-methylenedioxybenzyl)pyrimidine, lactose and corn starch are mixed in a suitable mixer.

2. The mixture is further blended by passing through a comminuting machine with a No. 1A screen with knives forward.

3. The blended powder is returned to the mixer, the talc added and blended thoroughly. The mixture is then filled into No. 4 hard shell gelatin capsules on a capsulating machine.

EXAMPLE 8

Tablet Formulation

|  | Per Tablet |
| --- | --- |
| N¹-(3,4-dimethyl-5-isoxazolyl)-sulfanilamide | 225 mg. |
| 2,4-Diamino-5-(3-methoxy-4,5-methylene-dioxybenzyl)pyrimidine | 60 mg. |
| Lactose | 233 mg. |
| Corn Starch | 100 mg. |
| Gelatin | 12 mg. |
| Talc | 15 mg. |
| Magnesium Stearate | 5 mg. |

Procedure:

1. 2,4-Diamino-5-(3-methoxy-4,5-methylenedioxybenzyl)pyrimidine, N¹-(3,4-dimethyl-5-isoxazolyl)sulfanilamide, corn starch and lactose are thoroughly mixed in suitable blending equipment and granulated with a 10 percent gelatin solution.

2. The moist mass is passed through a No. 12 screen, and the granules are dried on paper-lined trays overnight.

3. The dried granules are passed through a No. 14 screen and placed in a suitable mixer. The talc and magnesium stearate are added and blended.

4. The granulation is compressed into tablets weighing approximately 650 mg. each, using punches having an approximate diameter of 12.7 mm. (½ inch). The final tablet thickness is about 5.35 mm.

EXAMPLE 9

Tablet Formulation

|  | Per Tablet |
| --- | --- |
| Oxytetracycline | 225 mg. |
| 2,4-Diamino-5-(3-methoxy-4,5-methylene-dioxybenzyl)pyrimidine | 60 mg. |
| Lactose | 233 mg. |
| Corn Starch | 100 mg. |
| Gelatin | 12 mg. |
| Talc | 15 mg. |
| Magnesium Stearate | 5 mg. |

Procedure:

1. 2,4-Diamino-5-(3-methoxy-4,5-methylenedioxybenzyl)pyrimidine, oxytetracycline, corn starch and lactose are thoroughly mixed in suitable blending equipment and granulated with a 10 percent gelatin solution.

2. The moist mass is passed through a No. 12 screen, and the granules are dried on paper-lined trays overnight.

3. The dried granules are passed through a No. 14 screen and placed in a suitable mixer. The talc and magnesium stearate are added and blended.

4. The granulation is compressed into tablets weighing approximately 650 mg. each, using punches having an approximate diameter of 12.7 mm. (½ inch). The final tablet thickness is about 5.35 mm.

EXAMPLE 10

Suspension Formulation

|  | Gm. Per Liter |
| --- | --- |
| Methylparaben | 0.9 |
| Propylparaben | 0.5 |
| Sodium Edetate | 0.1 |
| Lactic Acid 85% | 8.3 cc. |
| 2,4-Diamino-5-(3-methoxy-4,5-methylene-dioxybenzyl)pyrimidine | 5.1 |
| Complex magnesium aluminum silicate | 26.4 |
| Sodium Benzoate | 2.5 |
| Sucrose | 400.0 |
| Sorbitol solution U.S.P. | 110.0 |
| Tragacanth | 3.5 |
| Methyl cellulose | 0.3 |
| Sorbitan monolaurate | 0.035 |
| N¹-(3,4-dimethyl-5-isoxazolyl)sulfanilamide Ultra Fine | 118.29 |
| Glycerin | 125.0 |
| FD and C Yellow No. 5 | 0.016 |
| Banana Flavor | 0.16 |
| NaOH — 40% Solution q.s. to pH 5.1 |  |
| Distilled Water q.s. | 1000.0 cc. |

Procedure:

1. The methyl and propyl parabens, sodium edetate and lactic acid are dissolved in 750 cc. of boiling distilled water. The 2,4-diamino-5-(3-methoxy-4,5-methylenedioxybenzyl)-pyrimidine is added with stirring.

2. The complex magnesium aluminum silicate is then added and cooked for 1 hour in a water bath at 80°–85°C.

3. The sodium benzoate is dissolved in 30 cc. of water and added to the mixture. The sucrose and sorbitol solution U.S.P. are then added.

4. The tragacanth is added to the glycerin with high shear and then added to the mixture with high mix.

5. The methyl cellulose is dissolved in 525 cc. of water, heated to 60°–65°C. and mixed for 10–15 minutes. The sorbitan monolaurate is dissolved in 15 cc. of heated water and added to the methyl cellulose solution. N¹-(3,4-dimethyl-5-isoxazolyl)sulfanilamide is added with high shear—when this is uniform, it is added to the mixture.

6. The colors and flavors are added when needed.

7. The pH is brought to 5.1 with 40% NaOH and the mixture brought to volume.

8. The mixture stands overnight before versating and homogenizing.

EXAMPLE 11

The unexpectedly increased antibacterial activity of antibiotics and, for example, N¹-(3,4-dimethyl-5-isoxazolyl)sulfanilamide, when combined with 2,4-diamino-5-(3-methoxy-4,5-methylenedioxybenzyl)-pyrimidine in the treatment of various bacterial infections was demonstrated utilizing the procedure set forth hereinbelow.

TABLE I (The antibacterial effect of N¹-(3,4-dimethyl-5-isoxazolyl)sulfanilamide in combination with e.g., 2,4-diamino-5-(3-methoxy-4,5-methylenedioxybenzyl)pyrimidine against bacterial infections in mice is set forth below.)

| Organism | Dose: mg/kg.[b] 2,4-diamino-5-(3-methoxy-4,5-methylenedioxybenzyl) pyrimidine | Increased Activity[a] of N¹-(3,4-dimethyl-5-isoxazole) sulfanilamide (x-fold potentiation) |
|---|---|---|
| D. pneumoniae No. 6301 | 50 | >11.9 |
|  | 25 | 11 |
|  | 10 | >2.3 |
| S. pyogenes 4 | 50 | >31.3 |
|  | 25 | 3.9 |
|  | 10 | 1.4 |
| S. aureus Smith | 5 | 2.1 |
| E. coli 257 | 10 | >5.7 |
| K. pneumoniae A | 5 | 2.3 |
| P. vulgaris 190 | 10 | 9.1 |
|  | 5 | 2.9 |
| S. typhosa P. 58a | 5 | 2.5 |

[a]Increased Activity (x-fold) = $\frac{\text{Dose Sulfonamide alone}}{\text{Dose Sulfonamide in Combination}}$

[b]These doses of 2,4-diamino-5-(3-methoxy-4,5-methylenedioxybenzyl)pyrimidine when administered alone are inactive.

TABLE II

The antibacterial effect of Penicillin or Oxytetracycline HCl in combination with 2,4-diamino-5-(3-methoxy-4,5-methylenedioxybenzyl)pyrimidine against bacterial infections in mice is set forth below.

| Organism | Dose: mg/kg.[b] 2,4-diamino-5-(3-methoxy-4,5-methylenedioxybenzyl) pyrimidine | Increased activity[a] of Penicillin (x-fold potentiation) | Increased activity[a] of Oxytetracycline HCl (x-fold potentiation) |
|---|---|---|---|
| D. pneumoniae No. 6301 | 50 | — | 4.0 |
| S. pyogenes 4 | 50 | — | 2.7 |
| E. coli 257 | 50 | 3 | 3.8 |
| S. schottmuelleri | 50 | >4.2 | 10.7 |

[a]Increased Activity (x-fold) = $\frac{\text{Dose Antibiotic alone}}{\text{Dose Antibiotic in combination}}$

[b]These doses of 2,4-diamino-5-(3-methoxy-4,5-methylenedioxybenzyl)pyrimidine when administered alone are inactive Swiss albino mice weighing 18 to 20 grams were infected intraperitoneally with 100 to 1000 minimal lethal doses of the organism. The inoculum was obtained from a properly diluted overnight broth culture. In all infections except D. pneumoniae, S. pyogenes and K. pneumoniae, the inoculum was finally diluted in 5 percent hog gastric mucin.

For all infections, the test animals were treated orally by gavage with 1.0 ml. of the desired concentration of the single drug or the appropriate sulfonamide-pyrimidine combination in 1 percent carboxymethylcellulose. Treatment consisted of a total of 6 doses. Two treatments, 5 hours apart, were administered on the day of and the day following infection and one treatment on the second and third days following infection. The first dose was administered 5–10 minutes after infection. When combinations were administered, varying concentrations of sulfonamide or antibiotic were prepared in the presence of an inactive concentration of a potentiator of the invention. The experimental observation period was 14 days. Heart blood from mice succumbing during this period of time was cultured on appropriate solid media to determine the presence or absence of the infecting organism.

Results obtained are given in Tables I and II.

We claim:

1. A therapeutic antibacterial composition comprising from about 1 to about 50 parts of oxytetracycline and one part of a pyrimidine of the formula

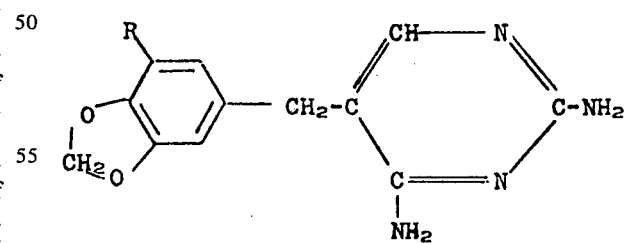

wherein R is lower alkoxy, or acid addition salts thereof with pharmaceutically acceptable acids.

2. A composition in accordance with claim 1, which contains pharmaceutical adjuvant materials.

3. A therapeutic antibacterial composition comprising from about 1 to 50 parts of oxytetracycline and one part of 2,4-diamino-5-(3-methoxy-4,5-methylenedioxybenzyl)pyrimidine.

* * * * *